(12) United States Patent
Leonardi et al.

(10) Patent No.: US 7,820,701 B2
(45) Date of Patent: Oct. 26, 2010

(54) AMORPHOUS LERCANIDIPINE HYDROCHLORIDE AND USES THEREOF

(75) Inventors: Amedeo Leonardi, Milan (IT); Gianni Motta, Barlassina (IT); Fabio Berlati, Milan (IT)

(73) Assignee: Recordati Ireland Limited, Cork (IL)

( * ) Notice: Subject to any disclaimer, the term of this patent is extended or adjusted under 35 U.S.C. 154(b) by 1240 days.

(21) Appl. No.: 11/364,862

(22) Filed: Feb. 27, 2006

(65) Prior Publication Data

US 2006/0211742 A1 Sep. 21, 2006

Related U.S. Application Data (60) Provisional application No. 60/656,836, filed on Feb. 25, 2005.

(51) Int. Cl.
C07D 211/82 (2006.01)
A61K 31/455 (2006.01)
(52) U.S. Cl. .................................. 514/355; 546/315
(58) Field of Classification Search ................ None
See application file for complete search history.

(56) References Cited

U.S. PATENT DOCUMENTS

| 4,705,797 | A | 11/1987 | Nardi |
|---|---|---|---|
| 4,968,832 | A | 11/1990 | Nardi |
| 5,696,139 | A | 12/1997 | Leonardi |
| 5,767,136 | A | 6/1998 | Sartani |
| 5,912,351 | A | 6/1999 | Leonardi |
| 6,852,737 | B2 | 2/2005 | Bonifacio et al. |
| 2003/0069285 | A1 | 4/2003 | Leonardi et al. |
| 2003/0083355 | A1 | 5/2003 | Bonifacio et al. |
| 2003/0180355 | A1 | 9/2003 | Leonardi et al. |
| 2004/0147566 | A1 | 7/2004 | Leonardi et al. |
| 2004/0198789 | A1 | 10/2004 | Leonardi et al. |
| 2005/0192323 | A1 | 9/2005 | Bonifacio et al. |
| 2005/0239847 | A1 | 10/2005 | Bonifacio et al. |
| 2006/0047125 | A1 | 3/2006 | Leonardi et al. |
| 2006/0073200 | A1 | 4/2006 | Leonardi et al. |

FOREIGN PATENT DOCUMENTS

WO WO-2006/046830 5/2006

*Primary Examiner*—Zinna N Davis
(74) *Attorney, Agent, or Firm*—Merchant & Gould PC (57) ABSTRACT

The invention provides a substantially pure amorphous lercanidipine hydrochloride having a purity of at least 95% pure, preferably at least about 97% pure, more preferably at least about 99% pure, and still more preferably at least about 99.5% pure. The invention further relates to methods of preparing substantially pure amorphous lercanidipine, as well as methods of providing rapid relief from hypertension by administering the substantially pure amorphous lercanidipine hydrochloride of the present invention to a patient in need of such treatment.

22 Claims, 2 Drawing Sheets

Figure 1. Powder X-ray diffraction patterns of crystalline (Ler3) and amorphous (Ler1) Lercanidipine HCl.

AMORPHOUS LERCANIDIPINE HYDROCHLORIDE AND USES THEREOF

This application claims the benefit of U.S. Provisional Patent Application No. 60/656,836, filed Feb. 25, 2005, which is hereby incorporated by reference in its entirety.

FIELD OF THE INVENTION

The invention provides a substantially pure amorphous lercanidipine hydrochloride and methods of preparing the same. The invention further relates to a method of providing rapid relief from hypertension by administering amorphous lercanidipine hydrochloride of the present invention to a patient in need of such treatment.

BACKGROUND OF THE INVENTION

Lercanidipine (methyl 1,1,N-trimethyl-N-(3,3-diphenyl-propyl)-2-aminoethyl 1,4-dihydro-2,6-dimethyl-4-(3-nitro-phenyl)pyridine-3,5-dicarboxylate) is a highly lipophilic dihydropyridine calcium antagonist with a long duration of action and high vascular selectivity. Lercanidipine's biological activity derives from its ability to competitively antagonize the dihydropyridine subunit of the L-type calcium channel.

Lercanidipine is useful as an anti-hypertensive. Lercanidipine lowers blood pressure by blocking calcium channels of arterial smooth muscle, thus decreasing peripheral vascular resistance. Lercanidipine produces no negative cardiac inotropism and only occasional mild reflex tachycardia, which is generally of short duration. Lercanidipine has been approved for the treatment of hypertension and has been marketed since 1996 in several European countries under the trademark Zanidip™.

The hydrochloride salt of lercanidipine is commercially available from Recordati S.p.A. (Milan, Italy). Methods of preparing lercanidipine hydrochloride, as well as methods of resolving lercanidipine into individual enantiomers are described in U.S. Pat. Nos. 4,705,797; 5,767,136; 4,968,832; 5,912,351; and 5,696,139, 6,852,737 and U.S. application, Publication No. 2003/0083355, all of which are incorporated herein by reference.

U.S. Pat. No. 4,705,797 described a process for the preparation of lercanidipine, the final step of the process being a cyclisation between 1,1,N-trimethyl-N-(3,3-diphenylpropyl)-2-aminoethyl α-acetyl-3-nitrocinnammate and methyl 3-aminocrotonate. The lercanidipine was isolated as its hydrochloride salt by crystallization from water containing HCl and NaCl. However, this process was expensive, time consuming, and resulted in relatively low yields of lercanidipine hydrochloride. Accordingly, the disclosed method was poorly suited for commercial production of amorphous lercanidipine hydrochloride.

In addition to being poorly suited for commercialization, the lercandipine produced by the method of the '797 patent was a crude ill-defined mixture of amorphous lercanidipine hydrochloride containing from 1% to 2% of crystalline lercanidipine hydrochloride. The product had a hydration ratio of from about 0.3:1 to 0.5:1, and contained less than 95% of lercanidipine hydrochloride (including that in crystalline form). Such a product is too impure for pharmaceutical use, and would require extensive further purification, e.g., by chromatography on different phases, before it would be suitable for such use. However, purification by these methods is costly and time consuming to be commercially applicable and thus unsuitable for commercial application.

Co-pending U.S. application Ser. No. 11/244,315 discloses that amorphous compositions, and in particular amorphous lercanidipine free base, are well suited for use in modified release capsules comprising waxy substances. To facilitate the development of lercanidipine pharmaceutical compositions, there remains a need in the art for amorphous lercanidipine hydrochloride that is suitable for formulation in pharmaceutical preparations. There further remains a need in the art for methods of producing the pharmaceutical grade amorphous lercanidipine hydrochloride that are more efficient than prior art methods of making amorphous lercanidipine hydrochloride, and which yields amorphous lercanidipine hydrochloride that is substantially pure, easily handled and easily incorporated into pharmaceutical compositions and oral dosage forms, and which is practicable for practicing on an industrial scale. Additionally, it is preferred that the resulting amorphous lercanidipine hydrochloride have similar or improved characteristics, e.g., solubility and bioavailability, compared to lercanidipine hydrochloride of the prior art.

To facilitate the development of new pharmaceutical compositions and solid dosage forms, the present inventors have discovered an improved method of preparing amorphous lercanidipine hydrochloride that is rapid, simple, well-suited for production on a commercial scale and yields a substantially pure product. The purified amorphous lercanidipine hydrochloride of the invention which can be prepared by methods of the invention is well suited for incorporation into pharmaceutical compositions and solid dosage forms, particularly modified release pharmaceutical dosage forms comprising a waxy matrix as a release modifying agent.

The inventors have also discovered that the amorphous lercanidipine of the present invention may be advantageously incorporated into immediate release pharmaceutical compositions that have improved pharmacokinetic properties and consequently provide rapid reduction in hypertension when administered to a patient. Amorphous lercanidipine hydrochloride begins exerting its activity to reduce blood pressure within a period of time following its administration that is markedly shorter than the time required for obtaining an effect following administration of crystalline lercanidipine hydrochloride.

SUMMARY OF THE INVENTION

The invention provides a substantially pure amorphous lercanidipine hydrochloride. The amorphous lercanidipine prepared as disclosed herein is substantially pure and has a greater aqueous solubility and faster onset of the antihypertensive effect when administered to a patient, compared to crystalline lercanidipine hydrochloride.

In another aspect the invention provides for a method of preparing amorphous lercanidipine hydrochloride and pharmaceutical compositions thereof, having improved dissolution profiles and different kinetic profile compared to crystalline lercanidipine hydrochloride. In a particular embodiment, the invention provides a method of preparing amorphous lercanidipine hydrochloride comprising (a) dissolving crystalline lercanidipine hydrochloride in an organic solvent at a first temperature in the range from about 30° C. to about 50° C. to form a first solution, adding the first solution to water at a temperature in the range from about 1° C. to about 20° C. to form a precipitate, maintaining the precipitate at a temperature in the range from about 1° C. to about 20° C., for a period from about 4 to about 24 hours, and recovering the amorphous lercanidipine hydrochloride.

In another specific embodiment, the present invention provides for a method of preparing an amorphous lercanidipine hydrochloride comprising the steps of dissolving crystalline lercanidipine hydrochloride in an organic solvent, rapidly evaporating the organic solvent, and recovering the amorphous lercanidipine hydrochloride.

In another aspect, the present invention provides for a method of providing rapid reduction in hypertension in a patient by administering to a patient in need thereof a therapeutically effective amount of substantially pure amorphous lercanidipine hydrochloride.

In another aspect, the present invention provides for a method or providing rapid reduction in hypertension in a patient by administering to a patient need thereof a composition consisting essentially of a therapeutically effective amount of substantially pure amorphous lercanidipine hydrochloride and a pharmaceutically acceptable excipient.

In still another embodiment, the present invention provides for rapid action pharmaceutical compositions and solid dosage forms, and in particular immediate release pharmaceutical compositions, comprising substantially purified amorphous lercanidipine hydrochloride.

DETAILED DESCRIPTION OF THE INVENTION

As used herein, the following terms are defined as follows:

The term "lercanidipine hydrochloride" refers to the hydrochloride salt of methyl 1,1,N-trimethyl-N-(3,3-diphenylpropyl)-2-aminoethyl 1,4-dihydro-2,6-dimethyl-4-(3-nitrophenyl)pyridine-3,5-dicarboxylate. The lercanidipine salt may be present as one or both of its enantiomeric forms.

The term "amorphous" refers to solid compounds having no substantial crystal lattice structure. Amorphous compounds typically yield DSC plots with broad endothermic transitions, defined as glass transitions. Crystalline compounds, by comparison, typically exhibit sharp exothermic peaks.

As used herein, the "substantially pure" refers to a composition that is at least 95% pure, preferably at least at least about 97% pure, and more preferably at least about 99% pure and still more preferably 99.5% pure on weight/weight basis relative to contaminants, including solvents carried over from the preparation of the composition.

The term "patient" refers to a mammal (e.g., a human) suffering from or at risk of developing the particular condition to be treated, e.g., essential hypertension, secondary hypertension, isolated systolic hypertension, coronary heart disease (e.g., chronic stable angina, myocardial infarction), congestive heart failure. In certain embodiments, the present invention is particularly applicable to patients suffering from hypertensive crisis or angina or other conditions where rapid vasodilation is indicated. Blood pressure may be measured, for example, by using a manual sphygmomanometer, automatic/electronic devices or ambulatory blood pressure monitoring.

The term "pharmaceutically acceptable" means compositions that are compatible for in vivo use. Preferred pharmaceutically acceptable compositions include compositions approved for use in animals, particularly humans, by a regulatory agency of the U.S., or a state government or listed in the U.S. Pharmacopoeia or other generally recognized pharmacopoeia.

The term "therapeutically effective amount" refers to the amount of active agent sufficient to lower the blood pressure of a patient with hypertension. Therapeutically effective amounts of active agent preferably lower blood pressure, such that the values for systolic and diastolic blood pressure are below 140 and 90 mm Hg, respectively. A therapeutically effective amount of the active agent may or may not decrease the blood pressure in a person that does not have hypertension or may not decrease blood pressure in all persons with hypertension. Therapeutic effectiveness in treatment of other pathologies, such as heart failure or atherosclerosis is also specifically contemplated as per, e.g., U.S. Pat. Nos. 5,696,139 and 5,767,136, which are incorporated herein by reference. Preferably, a therapeutically effective amount of active agent leads to a reduction in blood pressure, e.g., within about 2 to 6 hours. Preferably, when a rapid reduction in blood pressure is desired, a therapeutically effective amount of active agent will reduce systolic blood pressure in the range from about 20-30 mm Hg and diastolic blood pressure in the range from about 10-20 mm Hg, within about 30 minutes to about 60 minutes following administration of the active agent.

As used herein, the term "hypertension" refers to abnormally high arterial blood pressure, when compared to prior blood pressure readings, and the abnormally high value is maintained over a specified time period. Conventionally, the time period is in the range from about 3 to about 6 months. The increase may be observed in systolic pressure, diastolic pressure, or both. Conventionally, hypertension is defined as a blood pressure of equal to or greater than 140/90 mm Hg. Blood pressure may be measured by any method known in the art. Such methods include, but are not limited to direct arterial puncture, oscillometry, Doppler ultrasonography, and a sphygmomanometer. In a preferred embodiment, blood pressure is measured with a sphygmomanometer.

The term "systolic" as applied to blood pressure refers to the pressure induced upon contraction of the heart. The term "diastolic" as applied to blood pressure refers to the pressure induced upon dilatation of the cavities of the heart. Typically, blood pressure is expressed as two numbers separated by a slash, where the first number is the systolic pressure and the second number is the diastolic pressure. Blood pressure is conventionally expressed as millimeters of mercury (mm Hg).

Blood pressure in normal and hypertensive adults is typically categorized as follows:

| Category | Systolic Pressure, mmHg | Diastolic Pressure, mmHg |
|---|---|---|
| Normal | <120 | <80 |
| Prehypertension | 120–139 | 80–89 |
| Stage 1 Hypertension | 140–159 | 90–99 |
| Stage 2 Hypertension | >160 | >100 |

Source: The Seventh Report of the Joint National Committee on Prevention, Detection, Evaluation, and treatment of High Blood Pressure (JAMA, 289(19):2560-72 (2003))

Recent World Health Organization guidelines recommend a diastolic blood pressure lower than 85 mm Hg and a systolic blood pressure lower than 130 mm Hg in younger patients and in diabetic patients.

The term "antihypertensive activity" refers to the ability of an active agent to lower the blood pressure of a patient with hypertension.

The term "predetermined increment" refers to the minimum reduction in blood pressure that is needed for a patient to decrease blood pressure to or below a predetermined limit, preferably below 140/90.

The term "immediate release" means release of the active ingredient, e.g., amorphous lercanidipine hydrochloride, from a composition of the present invention resulting in in vivo release over a short period of time sufficient to provide therapeutically effective plasma levels over a similarly short time interval. Preferably, the release of lercanidipine provides for a maximum concentration of lercanidipine ($C_{max}$) of at least about 10 ng/mL and a time to maximum plasma concentration ($T_{max}$) in the range from about 45 to about 75 minutes for a 20 or 40 mg dose of amorphous lercanidipine hydrochloride when administered to a human patient.

The terms "treat" and "treating" refer to reducing or relieving hypertension, e.g., decreasing either systolic or diastolic blood pressure in a patient by at least about 5 mm Hg, preferably by at least about 10 mm Hg, and more preferably by at least about 15 mm Hg.

Preparation of Amorphous Lercanidipine Hydrochloride

The present invention provides a substantially pure amorphous lercanidipine hydrochloride, particularly an amorphous lercanidipine hydrochloride having a purity of at least about 95% and more preferably at least about 97%, even more preferably at least about 99% and still more preferably at least about 99.5%. The purity of the amorphous lercanidipine of the present invention may be determined by any method known in the art, including, but not limited to high performance liquid chromatography (HPLC) analysis. The amorphous lercanidipine hydrochloride preferably contains less than 0.5% of crystalline lercanidipine hydrochloride, and is more preferably free or substantially free of crystalline lercanidipine hydrochloride.

The present invention provides methods of preparing amorphous lercanidipine hydrochloride. The methods disclosed herein yield amorphous lercanidipine hydrochloride in a substantially purer state, having improved solubility and different pharmacokinetics properties compared to those of other known forms of lercanidipine hydrochloride and compared to previously known forms of amorphous lercanidipine hydrochloride. The amorphous lercanidipine hydrochloride of the present invention is easily incorporated into pharmaceutical compositions and solid dosage forms.

In one embodiment, amorphous lercanidipine hydrochloride is prepared by precipitation from purified crystalline lercanidipine hydrochloride. Preferably the precipitation reaction is carried out by first dissolving a crystalline lercanidipine hydrochloride in an organic solvent at a first temperature in the range from about 30° C. to about 50° C. to form a first solution and then adding the first solution to water at a second temperature in the range from about 1° to about 20° C. to form a precipitate. The precipitate is maintained at the second temperature from about 4 hours to about 24 hours, followed by recovery of amorphous lercanidipine hydrochloride.

Preferred organic solvents include, but are not limited to polar protic or aprotic solvents, and mixtures thereof. Examples of suitable solvents include, but are not limited to water miscible solvents such as alcohols, preferably ($C_1$-$C_6$)-alkanols, acetone, chlorinated solvents, such as dichloromethane, and amides, such as dimethylformamide. Particularly preferred solvents include methanol or mixtures of methanol and ethanol.

In another embodiment, amorphous lercanidipine hydrochloride is prepared by evaporation. Preferably a solution of crystalline lercanidipine hydrochloride is prepared by dissolving the hydrochloride salt in an organic solvent. Preferred organic solvents include, but are not limited to polar protic and aprotic solvents, such as alcohols, preferably lower alkyl alcohols, chlorinated solvents, such as dichloromethane and mixtures thereof. One particularly preferred solvent is methanol. The solvent is then removed from the solution by evaporation, using techniques well known in the art. For example, without limitations, evaporation under vacuum. Evaporation is preferably carried out a temperature in the range from about 20° C. to about 40° C. and most preferably at a temperature of about 30° C.

Pharmaceutical Compositions

Amorphous lercanidipine hydrochloride prepared by the methods disclosed herein may be formulated into pharmaceutical compositions. In one embodiment, the present invention provides a pharmaceutical composition consisting essentially of a therapeutically effective amount of substantially pure amorphous lercanidipine hydrochloride, and at least one component selected from the group consisting of a pharmaceutically acceptable carrier or diluent, flavorant, sweetener, preservative, dye, binder, suspending agent, dispersing agent, colorant, disintegrant, excipient, film forming agent, lubricant, plasticizer, edible oil, and a binder. In a preferred embodiment, the pharmaceutical composition or dosage form comprises about 0.1 to 400 mg amorphous lercanidipine hydrochloride, for all uses disclosed herein. Preferably, the composition or dosage form comprises from about 1 to 200 mg amorphous lercanidipine hydrochloride, more still more preferably from about 5 to 40 mg.

Suitable pharmaceutically acceptable carriers or diluents include, but are not limited to, ethanol, water, glycerol, propylene glycol, aloe vera gel, allantoin, lactose, microcrystalline cellulose, mannitol, sodium phosphate, calcium phosphate, sugar, fructose, glucose, sorbitol, glycerin, vitamin A and E oils, mineral oil, PPG2 myristyl propionate, magnesium carbonate, potassium phosphate, vegetable oil, animal oil, and solketal.

Suitable disintegrants include, but are not limited to, starch, e.g., corn starch, sodium starch glycolate, sodium crosscarmellose, methyl cellulose, agar, bentonite, xanthan gum, sodium starch glycolate, crosspovidone and the like.

Suitable lubricants include, but are not limited to, sodium oleate, sodium stearate, sodium stearyl fumarate, magnesium stearate, stearic acid, sodium benzoate, sodium acetate, sodium chloride and the like.

A suitable film forming agent is, but is not limited to, hydroxypropyl methyl cellulose (hypromellose), ethyl cellulose, shellac, sucrose, acrylic acids derivatives (e.g. methacrylic acid copolymer, ammonio methacrylate copolymer), or mixtures of two or more of these substances, and the like.

Suitable dispersing and suspending agents include, but are not limited to, synthetic and natural gums, such as vegetable gum, tragacanth, acacia, alginate, dextran, sodium carboxymethylcellulose, methylcellulose, polyvinyl-pyrrolidone, bentonite, ethoxylated isostearyl alcohols, polyoxyethylene sorbitol and sorbitan esters, microcrystalline cellulose, aluminum metahydroxide, agar-agar and gelatin.

Anti-adherents and glidants Include, but are not limited to, talc, calcium silicate, magnesium silicate, colloidal silicon dioxide.

Suitable plasticizers include, but are not limited to, polyethylene glycols of different molecular weights (e.g., 200-8000 Da), triethyl citrate and propylene glycol.

Suitable colorants include, but are not limited to, ferric oxide(s), titanium dioxide and natural and synthetic lakes.

Suitable edible oils include, but are not limited to, cottonseed oil, sesame oil, coconut oil and peanut oil.

Suitable binders include, but are not limited to, either individually or in combination, sucrose; gelatin; glucose; starch; cellulose materials such as, but not limited to, methylcellulose and sodium carboxymethylcellulose; alginic acid and salts of alginic acid; magnesium aluminum silicate; polyethylene glycol; guar gum; polysaccharide acids; bentonites; polyvinylpyrrolidone (povidone); polymethacrylates (such as Eudragit™); hydroxypropyl methylcellulose (HPMC); hydroxypropyl cellulose (Klucel™); ethyl cellulose (Ethocel™); pregelatinized starch (e.g., National™ 1511 and Starch 1500).

Examples of additional additives include, but are not limited to, sorbitol, talc, stearic acid, dicalcium phosphate and polydextrose.

The pharmaceutical compositions of the present invention may optionally include a film coating layer. The coating layer may consists of a film forming agent, a plasticizer, an anti-adherent agent and colorants. However, any coating known in the art may be used.

The pharmaceutical compositions of the present invention may preferably comprises amorphous lercanidipine hydrochloride in any amount from about 0.001 to about 0.2 mg per mg of the total composition, and more preferably from about 0.005 mg to about 0.15 mg per mg of the total composition and most preferably from about 0.01 mg to about 0.1 mg per mg of the total composition. Preferably a pharmaceutical compositions of the present invention has a weight in the range from about 50 to about 400 mg and comprises an amount of amorphous lercanidipine hydrochloride in the range from about 5 to about 40 mg, but amounts up to about 80 mg of active agent are contemplated.

In a preferred embodiment, the pharmaceutical composition is an immediate release composition comprising the amorphous lercanidipine hydrochloride of the present invention admixed with soluble and insoluble components, such as carriers, disintegrants, binders, and lubricants. Preferably upon administration to a patient, the immediate release compositions of the present invention results in a rapid rise in the plasma concentration of lercanidipine. Preferably administration of the immediate release compositions results in a maximum plasma concentration of lercanidipine of at least about 10 ng/mL ($C_{max}$) in a time interval in the range from about 45 to about 75 minutes ($T_{max}$).

In a preferred embodiment, the immediate release composition comprises a carrier, a disintegrant, a lubricant and a binder. The carrier component may be one or more of the aforementioned water soluble and/or insoluble carriers. Preferred water soluble carriers include, for example a sugar, such as sucrose, lactose, fructose, or mannitol. Preferred water insoluble carriers include, for example, microcrystalline cellulose. The disintegrant may be any one of the aforementioned disintegrants, and preferably sodium starch glycolate. The binder may be any one of the aforementioned binders, and preferably polyvinylpyrrolidone (povidone). The lubricant may be any one of the aforementioned lubricants, and preferably magnesium stearate.

The immediate release compositions may be formed by depositing a mixture of the active agent and soluble and insoluble components on inert cores. The mixture may be deposited by wet massing and extrusion, granulation, spray drying or deposited using other methods known in the art. Additionally, the mixture may be used in the preparation of a suspension, filled into capsules, pressed into tablets or filled into sachets.

The immediate release composition may optionally include a film coating to improve the durability, appearance and/or handling of the composition. Preferably the film coating does not interfere with the dissolution and/or pharmacokinetic properties of the immediate release composition. Examples of film coatings contemplated by the present invention include, but are not limited to, those that include hydroxypropylmethyl cellulose and polymethacrylates. However, any coating known in the art may be used.

The immediate release pharmaceutical compositions may also optionally include additional excipients to improve appearance, handling and processing properties and/or dissolution properties of the active ingredient. Additional excipients contemplated by the present invention include, but are not limited to, carriers, diluents, disintegrants, lubricants, glidants and/or anti-adherent agents.

In another embodiment the amorphous lercanidipine hydrochloride of the present invention may be incorporated into modified release compositions comprising amorphous lercanidipine hydrochloride and a waxy substance. The modified release lercanidipine pharmaceutical compositions provide for modified release of lercanidipine over an extended period of time providing an increased mean plasma concentration of amorphous lercanidipine hydrochloride over the dosing duration, compared to commercially available lercanidipine hydrochloride immediate release tablets. In particular, when administered to a patient, the present compositions result in a mean plasma concentration of lercanidipine of greater than about 0.5 ng/mL for at least about 24 hours following administration.

The term "waxy substance" refers to a plastic solid substance with a low melting point. "Waxy substance" may refer to one type of compound or a mixture of different compounds, as context requires. Waxy substances may be lipophilic or hydrophilic. Preferred waxy substances are polyalcohol fatty acyl esters, e.g., polyethylene glycol, polypropylene glycol esters and fatty acid glycerides, and combination thereof. More preferred waxy substances are polyglyocolized glycerides.

The term "solid" as used herein refers to a substance that is solid or semi-solid at room temperature. Hence, as used herein, a "solid" substance may become liquid at, e.g., body temperature.

Fatty acid glycerides suitable for use in modified release formulations include both medium chain and long chain fatty acid glycerides. In one aspect, the pharmaceutical compositions of the present invention may include one or more long chain ($C_{12}$ to $C_{22}$) fatty acid glycerides (including monoesters, diesters and/or triesters of glycerol). Examples of long chain fatty acid glycerides, within the scope of the present invention are Compritol 888 ATO™ and Precirol ATO 5™ (commercially available from Gattefossé Corporation, Paramus, N.J.)

Additional preferred fatty acid glycerides, suitable for use herein include one or more medium chain ($C_8$ to $C_{11}$) fatty acid glycerides such as one or more triglycerides of $C_8$ to $C_{11}$ fatty acids. One example of one medium chain fatty acid triglyceride, within the scope of the present invention is Miglyol™ 812 (commercially available from Condea Chemie GmbH, Cranford, N.J.).

Polyethylene glycol esters and polypropylene esters suitable for use in modified release formulations include mono- and diesters of polyethylene glycols and polypropylene glycols. Suitable and preferred fatty acids for inclusion in polyethylene glycol esters and polypropylene glycol esters are $C_{12}$ to $C_{22}$ fatty acids, as set forth above. Suitable polyethylene glycol chains and polypropylene chains for use respectively in polyethylene glycol esters and polypropylene glycol esters are described in, e.g., the U.S. Pharmacopeia.

Preferred fatty acid glycerides for use in the present modified release compositions, have a melting point from about 40° C. to about 80° C. and a HLB value from about 1 to about 14.

"Polyglycolized glycerides" denotes a mixture of mono-, di- and triglycerides and polyethylene glycol (PEG) mono- and diesters. Polyglycolized glycerides are particularly preferred waxy substances for use in the present invention. Polyglycolized glycerides are commercially available under the name Gelucire™ (Gattefossé Corporation, Paramus, N.J.).

In another embodiment the amorphous lercanidipine hydrochloride of the present invention may be incorporated into modified release compositions comprising amorphous lercanidipine hydrochloride and a release modifying matrix comprising a hydrophilic polymer. The modified release lercanidipine pharmaceutical compositions provide for modified release of lercanidipine over an extended period of time providing an increased mean plasma concentration of lercanidipine over the dosing duration, compared to commercially available lercanidipine immediate release tablets. In particular, when administered to a patient, the present compositions result in a mean plasma concentration of lercanidipine of greater than about 0.5 ng/mL for at least about 24 hours following administration.

In another embodiment, the modified release composition comprises an inert core, amorphous lercanidipine hydrochloride and a hydrophilic polymer. The term "hydrophilic polymer" refers to a solid polymeric substance with a low melting point. The hydrophilic polymer may be either a single polymeric entity or a mixture of two or more polymers, depending on the desired modified release properties. Exemplary hydrophilic polymers may be found among tablet binders, suspending or viscosity increasing agents, and film forming agents. Preferred hydrophilic polymers are cellulose derivative, for example, hydroxypropyl methyl cellulose, ethyl cellulose, methyl cellulose, sodium carboxymethyl cellulose and combination thereof. More preferred hydrophilic polymers are hydroxypropyl methyl cellulose derivatives.

The modified release composition may optionally include a film coating to improve the durability, appearance and/or handling of the composition. Preferably the film coating does not interfere with the dissolution and/or pharmacokinetic properties of the modified release composition. Examples of film coatings contemplated by the present invention include, but are not limited to, those that include hydroxypropylmethyl cellulose or polymethacrylates. However, any coating known in the art may be used.

Unit Dosage Forms

The pharmaceutical composition may be formulated as unit dosage forms, such as tablets, pills, capsules, caplets, boluses, powders, granules, sterile parenteral solutions, sterile parenteral suspensions, sterile parenteral emulsions, elixirs, tinctures, metered aerosol or liquid sprays, drops, ampoules, autoinjector devices or suppositories. Unit dosage forms may be used for oral, parenteral, intranasal, sublingual or rectal administration, or for administration by inhalation or insufflation, transdermal patches, and a lyophilized composition. In general, any delivery of active ingredients that results in systemic availability of them can be used. Preferably the unit dosage form is an oral dosage form, most preferably a solid oral dosage form, therefore the preferred dosage forms are tablets, pills, caplets and capsules. Parenteral preparations also are preferred.

Solid unit dosage forms may be prepared by mixing an active agent of the present invention with a pharmaceutically acceptable carrier and any other desired additives as described above. The mixture is typically mixed until a homogeneous mixture of the active agents of the present invention and the carrier and any other desired additives is formed, i.e., until the active agent is dispersed evenly throughout the composition. In this case, the compositions can be formed as dry or moist granules.

Tablets or pills can be coated or otherwise compounded to form a unit dosage form which has delayed and/or prolonged action, such as time release and sustained release unit dosage forms. For example, the tablet or pill can comprise an inner dosage and an outer dosage component, the latter being in the form of a layer or envelope over the former. The two components can be separated by an enteric layer which serves to resist disintegration in the stomach and permits the inner component to pass intact into the duodenum or to be delayed in release.

Biodegradable polymers for controlling the release of the active agents, include, but are not limited to, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For liquid dosage forms, the active substances or their physiologically acceptable salts are brought into solution, suspension or emulsion, optionally with the usually employed substances such as solubilizers, emulsifiers or other auxiliaries. Solvents for the active combinations and the corresponding physiologically acceptable salts, can include water physiological salt solutions or alcohols, e.g., ethanol, propane-diol or glycerol. Additionally, sugar solutions such as glucose or mannitol solutions may be used. A mixture of the various solvents mentioned may further be used in the present invention.

A transdermal dosage form also is contemplated by the present invention. Transdermal forms may be a diffusion-driven transdermal system (transdermal patch) using either a fluid reservoir or a drug-in-adhesive matrix system. Other transdermal dosage forms include, but are not limited to, topical gels, lotions, ointments, transmucosal systems and devices, and iontophoretic (electrical diffusion) delivery system. Transdermal dosage forms may be used for timed release and sustained release of the active agents of the present invention.

Pharmaceutical compositions and unit dosage forms of the present invention for administration parenterally, and in particular by injection, typically include a pharmaceutically acceptable carrier, as described above. A preferred liquid carrier is vegetable oil. Injection may be, for example, intravenous, intrathecal, intramuscular, intraruminal, intratracheal, or subcutaneous.

The active agent also can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The amorphous lercanidipine hydrochloride may be coupled with soluble polymers as targetable drug carriers. Such polymers include, but are not limited to, polyvinylpyrrolidone, pyran copolymer, polyhydroxypropylmethacryl-amidephenol, polyhydroxyethylaspartamide-phenol, and polyethyleneoxideopolylysine substituted with palmitoyl residues.

Administration

The pharmaceutical composition or unit dosage forms of the present invention may be administered by a variety of routes such as intravenous, intratracheal, subcutaneous, oral, mucosal parenteral, buccal, sublingual, ophthalmic, pulmonary, transmucosal, transdermal, and intramuscular. Unit dosage forms also can be administered in intranasal form via topical use of suitable intranasal vehicles, or via transdermal routes, using of transdermal skin patches known to those of ordinary skill in the art. Oral administration is preferred.

The pharmaceutical composition or unit dosage forms of the present invention may be administered to an animal, preferably a human being, in need of antihypertensive treatment. The pharmaceutical composition or unit dosage form of the present invention may be administered according to a dosage and administration regimen defined by routine testing in light of the guidelines given above in order to obtain optimal antihypertensive activity and a decreased in blood pressure while minimizing toxicity or side-effects for a particular patient. However, such fine turning of the therapeutic regimen is routine in light of the guidelines given herein.

The dosage of the composition containing amorphous lercanidipine hydrochloride of the present invention may vary according to a variety of factors such as underlying disease state, the individual's condition, weight, sex and age and the mode of administration. For oral administration, the pharmaceutical compositions can be provided in the form of scored or unscored solid unit dosage forms.

The pharmaceutical composition or unit dosage form may be administered in a single daily dose, or the total daily dosage may be administered in divided doses. In addition, co-administration or sequential administration of other active agents may be desirable. The amorphous form thereof of the invention may be combined with any known drug therapy, preferably for treatment of hypertension. For example, an immediate release composition of the present invention may be combined with an ACE inhibitor, such as enalapril, described in U.S. published application no. 2003/00180355, or with lisinopril as described in commonly-owned U.S. published application no. 2004/0147566. Lercanidipine may also be combined with an angiotensin II receptor blocker (ARB), as disclosed in U.S. published application no. 2004/0198789, for example. Also contemplated by the present invention is addition of a diuretic or a receptor blocker to the lercanidipine formulation. Exemplary diuretics include thiazide diuretics, potassium sparing diuretics, loop diuretics, such as hydrochlorothiazide, spironolactone, and ethacrynic acid, respectively.

For combination therapy the compounds may initially be provided as separate dosage forms until an optimum dosage combination and administration regimen is achieved. Therefore, the patient may be titrated to the appropriate dosages for his/her particular hypertensive condition. After the appropriate dosage of each of the compounds is determined to achieve a decrease of the blood pressure without untoward side effects, the patient then may be switched to a single dosage form containing the appropriate dosages of each of the active agents, or may continue with a dual dosage form.

The exact dosage and administration regimen utilizing the combination therapy of the present invention is selected in accordance with a variety of factors including type, species, age, weight, sex and medical condition of the patient; the severity and etiology of the hypertension to be treated; the route of administration; the renal and hepatic function of the patient; the treatment history of the patient; and the responsiveness of the patient. Optimal precision in achieving concentrations of compounds within the range that yields efficacy without toxicity requires a regimen based on the kinetics of the drug's availability to target sites. This involves a consideration of the absorption, distribution, metabolism, excretion of a drug, and responsiveness of the patient to the dosage regimen. However, such fine tuning of the therapeutic regimen is routine in light of the guidelines given herein.

Generally, a dosage forms for parenteral administration contains not below 0.1%, preferably from about 0.5% to about 30%, by weight of amorphous lercanidipine, based upon the total weight of the dosage form. Transdermal dosage forms contain from about 0.01% to about 100% by weight of the active agents, based upon 100% total weight of the dosage.

In a preferred embodiment of the present invention, the composition is administered daily to the patient. In a further preferred embodiment, the pharmaceutical composition or dosage form is administered daily in an amount in the range from about 0.1 to 400 mg of amorphous lercanidipine hydrochloride, more preferably from about 1 to 200 mg, and even more preferably from about 5 to 40 mg.

Preferably upon administration of the substantially pure amorphous lercanidipine hydrochloride of the present invention, a patient's blood pressure is reduced rapidly by a predetermined increment. Preferably the reduction of systolic blood pressure is in the range from about 20 to about 30 mm Hg, and most preferably about 25 mm Hg, following the administration of 20 mg of amorphous lercanidipine hydrochloride. Preferably the reduction of diastolic blood pressure is in the range from about 10 to about 20 mm Hg, and most preferably about 15 mm Hg, following the administration of 20 mg of amorphous lercanidipine.

In other aspects, administration of substantially pure amorphous lercanidipine hydrochloride provides rapid reduction in hypertension in a patient following administration. Preferably, administration of a therapeutically effective amount of the substantially pure amorphous lercanidipine hydrochloride of the present invention results in a rapid rise in the plasma concentration of lercanidipine, such that the maximum plasma concentration of lercanidipine ($C_{max}$) is in the range from about 10 to about 20 ng/mL in a period of time from about 45 to about 75 minutes ($T_{max}$) following administration of the active agent. Still more preferably, administration of a therapeutically effective amount of amorphous lercanidipine hydrochloride of the present invention results in a $C_{max}$ of at least about 10 ng/mL and a $T_{max}$ of about 1 hour.

EXAMPLES

The following examples are illustrative in nature of the various aspects of the present invention and are not intended to be limiting in any manner.

Example 1

Preparation of Amorphous Lercanidipine Hydrochloride by Precipitation

Crystalline lercanidipine hydrochloride (500 g; Recordati, S.p.A., Milan Italy) was dissolved in 1 liter of methanol with heating from about 35 to about 40° C. A temperature controlled cylindrical reactor, equipped with a mechanical stirrer, Gooch Filter and dropping funnel, was cooled to between 0 and 5° C. The warm crystalline lercanidipine hydrochloride/methanol solution was added dropwise to the reactor using the funnel, over a period of not less than 6 hours, while maintaining the reactor at about 5° C. The resulting suspension was stirred for about 16 hours at a temperature between about 2 and 5° C. The resulting suspension was filtered under vacuum through the Gooch filter. The solid obtained was dried in an air stream at room temperature for 48 hours followed by vacuum drying at 70° C. for 30 hours to yield amorphous lercanidipine hydrochloride (72.8% yield), HPLC assay: 99.6%.

The resulting substantially pure amorphous lercanidipine hydrochloride was micronized by a jet-mill process using a MICRONETTE M300 (Nuova Guseo, Villanova sull'Arda-PC-Italy). Micronization parameters were as follows: Injection pressure, 5 Kg/cmq; micronization pressure, 9 Kg/cmq; and cyclone pressure, 2.5 Kg/cmq. Capacity of micronization is 16 Kg/h. Particle size was determined by laser light scattering using a GALAI CIS 1 laser instrument (Galai, Haifa, Israel). Micronization was performed to obtain an average particle size of D (50%) 2-8 Jim and D (90%) <15 μm.

The resulting amorphous lercanidipine hydrochloride was subjected to melting point analysis using open capillary method The resulting melting point is shown in Table 1.

TABLE 1

Comparison of Crystalline and Amorphous Lercanidipine

| SAMPLE | MP (° C.) | SOLUBILITY (mg/L) |
|---|---|---|
| Amorphous lercanidipine HCl (Example 1) | 119–123 | 1.5 |
| Amorphous lercanidipine HCl (Example 2) | 119–123 | 1.5 |
| Crystalline lercanidipine HCl (Form I) | 186–188 | 0.65 |

Example 2

Preparation of Amorphous Lercanidipine HCl by Evaporation

Crystalline lercanidipine hydrochloride (40 g; Recordati, S.p.A., Milan Italy) was dissolved in 2.8 liters in either methanol or dichloromethane at a temperature from about 35° C. to about 40° C. Solvent was removed by drying overnight under vacuum (1 mm Hg) using a rotary evaporator at 30° C. The resulting solid was further dried under vacuum (1 mm Hg) at 50° C. to yield amorphous lercanidipine hydrochloride.

The resulting amorphous lercanidipine hydrochloride was subjected to melting point analysis using the open capillary method. The resulting melting points are reported in Table 1, above.

The aqueous solubility of amorphous lercanidipine hydrochloride, was compared to the solubility of crystalline lercanidipine hydrochloride. The solubility of the respective samples was determined by suspending 20-30 mg of sample test was in 10 mL water and stirring at 27-28° C. for 24 hr. The sample was then filtered through a PVDF filter (0.2 micron) and the solution diluted with acetonitrile and analyzed by HPLC. The results are shown in Table 1, above.

Example 3

Pharmacokinetic Properties of Amorphous Lercanidipine HCl Compared to Crystalline Lercanidipine HCl The bioavailability of amorphous lercanidipine hydrochloride was compared to commercially available crystalline lercanidipine hydrochloride (Zanidip™, Recordati, Milan, Italy) in dogs. Four male beagle dogs were administered 5 mg/kg of amorphous micronized lercanidipine hydrochloride, prepared as described in Example 1 or 5 mg/kg of crystalline lercanidipine hydrochloride in a randomized order. Amorphous and crystalline lercanidipine hydrochloride was formulated as immediate release tablets as described below in Tables 2 and 3. There was one week wash-out between each period.

TABLE 2

Lercanidipine Hydrochloride 10 mg filmed tablets

| Ingredients | Amount mg/tablet |
|---|---|
| Active substance | |
| Lercanidipine hydrochloride | 10.0 |
| equivalent to lercanidipine | 9.4 |
| Excipients | |
| Core | |
| Lactose monohydrate | 30.0 |
| Microcrystalline cellulose | 39.0 |
| Sodium starch glycolate (type A) | 15.5 |
| Povidone K 30 | 4.5 |
| Magnesium stearate | 1.0 |
| Coating | |
| Opadry OY-SR-6497 | 3.0 |
| corresponding to: | |
| Hypromellose | (1.913) |
| Talc | (0.150) |
| Titanium dioxide | (0.600) |
| Macrogol 6000 | (0.300) |
| Ferric oxide | (0.037) |
| Total weight | 103.0 |

TABLE 3

Lercanidipine Hydrochloride 20 mg filmed tablets

| Ingredients | Amount mg/tablet |
|---|---|
| Active substance | |
| Lercanidipine hydrochloride | 20.0 |
| equivalent to lercanidipine | 18.8 |
| Excipients | |
| Core | |
| Lactose monohydrate | 60.0 |
| Microcrystalline cellulose | 78.0 |
| Sodium starch glycolate (type A) | 31.0 |
| Povidone K 30 | 9.0 |
| Magnesium stearate | 2.0 |

TABLE 3-continued

Lercanidipine Hydrochloride 20 mg filmed tablets

| Ingredients | Amount mg/tablet |
|---|---|
| Coating | |
| Opadry 02F25077 corresponding to: | 6.0 |
| Hypromellose | (3.825) |
| Talc | (0.300) |
| Titanium dioxide | (1.200) |
| Macrogol 6000 | (0.600) |
| Ferric oxide | (0.075) |
| Total weight | 206.0 |

Blood samples were taken at given times and plasma concentrations of lercanidipine were determined with a validated stereoselective analytical method LC-MS/MS. Lercanidipine was extracted from dog plasma by means of liquid-liquid extraction with a mixture of n-hexane and diethyl ether followed by evaporation of the solvent under nitrogen. The resulting dry residue was taken up with a mixture of methanol and water. The two enantiomers of lercanidipine were separated on a Chirobiotic V column (Vancomycin) (particle size 5 μm, column size 150×4.6 mm (ASTEC, Whippany, N.J.) and were detected with a mass spectrometer (MS/MS) using an electrospray technique. The analytical method was validated in a concentration range between 0.2 and 20 ng/mL of plasma for both enantiomers. The method has shown to be specific with an accuracy of 15%.

Figure 1:
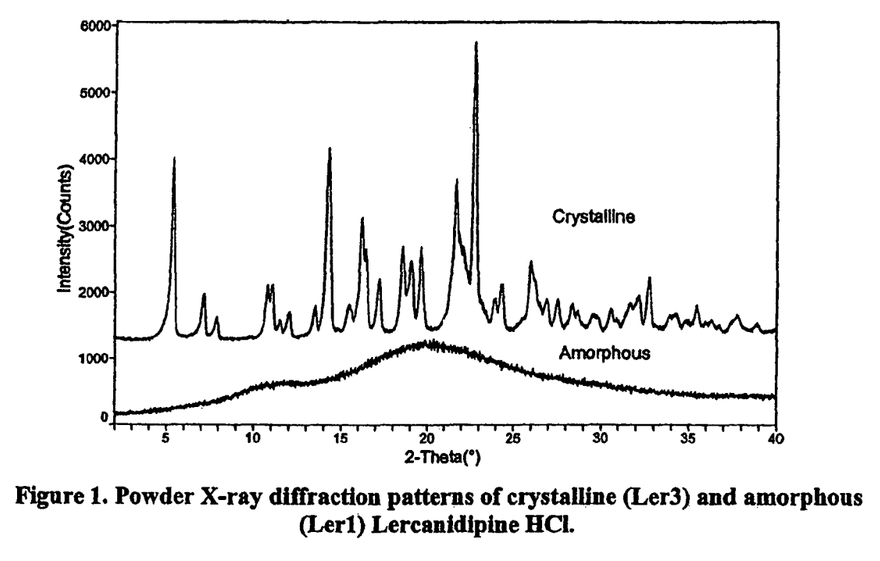
FIG. 1 is a comparison of the X-ray powder diffraction spectra of crystalline lercanidipine hydrochloride (form I and form II) and amorphous lercanidipine hydrochloride.
Figure 2:
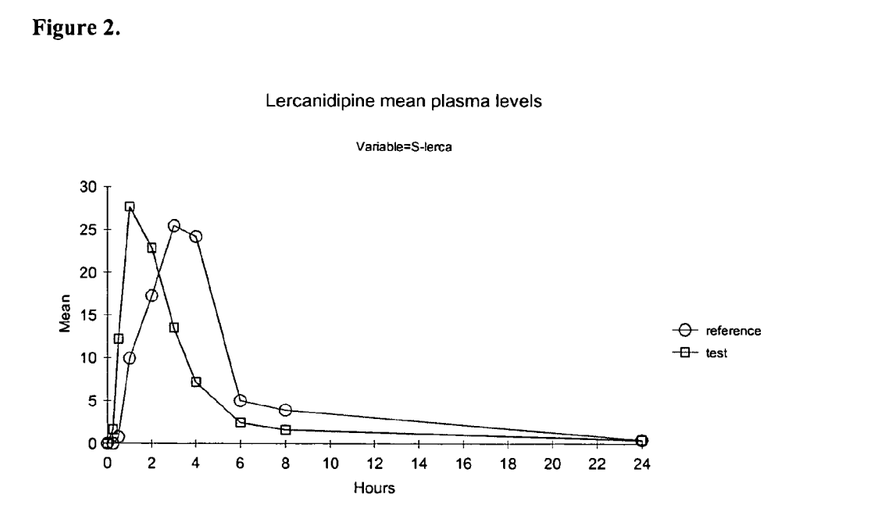
FIG. 2 depicts in vivo S-lercanidipine plasma concentrations following administration of 5 mg/kg of amorphous lercanidipine hydrochloride (-□-), and 5 mg/kg crystalline lercanidipine hydrochloride (-○-) to the subject.
Figure 3:
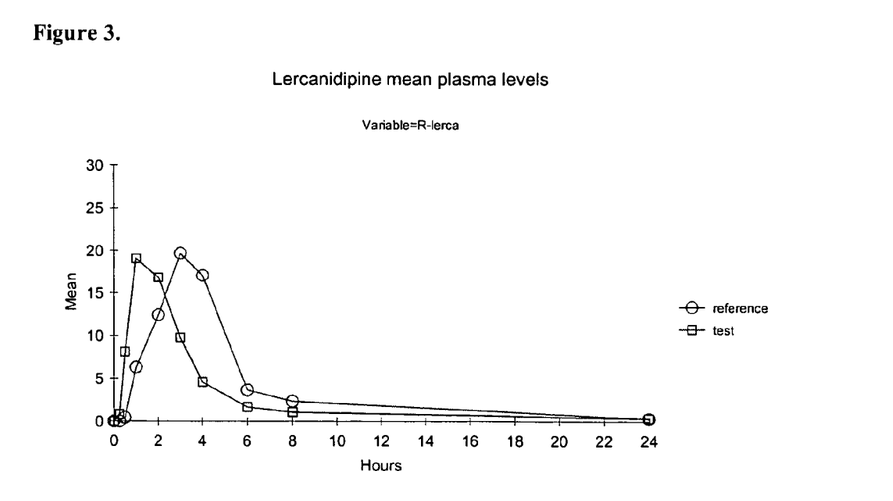
FIG. 3 depicts in vivo R-lercanidipine plasma concentrations following administration of 5 mg/kg of amorphous lercanidipine hydrochloride (-□-), and 5 mg/kg crystalline lercanidipine hydrochloride (-○-) to the subject.

The mean plasma levels of S- and R-lercanidipine for both forms are shown in FIGS. 2 and 3. The pharmacokinetic data are summarized in the tables below.

TABLE 4

Comparative pharmacokinetic data for S- lercanidipine hydrochloride amorphous form and crystalline lercanidipine hydrochloride

| Sample | $AUC_{last}$ (ng * h/mL) | $C_{max}$ (ng/mL) | $T_{max}$ (h) |
|---|---|---|---|
| Amorphous | 91.72 ± 58.59 | 31.09 ± 22.06 | 1.0 |
| Crystalline | 117.71 ± 87.20 | 39.19 ± 34.42 | 2.0 |

TABLE 5

Comparative pharmakokinetic data for R- lercanidipine hydrochloride amorphous form and crystalline lercanidipine hydrochloride

| Sample | $AUC_{last}$ (ng * h/mL) | $C_{max}$ (ng/mL) | $T_{max}$ (h) |
|---|---|---|---|
| Amorphous | 63.92 ± 41.80 | 22.76 ± 15.80 | 1.0 |
| Crystalline | 82.40 ± 67.61 | 28.57 ± 26.39 | 2.0 |

The present invention is not to be limited in scope by the specific embodiments described herein. Various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed:

1. Substantially pure amorphous lercanidipine hydrochloride having a purity of at least 95%.

2. The substantially pure amorphous lercanidipine hydrochloride of claim 1, having a purity of at least about 99%.

3. The substantially pure amorphous lercanidipine hydrochloride of claim 1, having a purity of at least about 99.5%.

4. A pharmaceutical composition consisting essentially of a therapeutically effective amount of substantially a pure amorphous lercanidipine hydrochloride having a purity of at least 95% and a pharmaceutically acceptable excipient.

5. A method of providing rapid reduction of blood pressure in a patient in need thereof, comprising administering to said patient a therapeutically effective amount of amorphous lercanidipine hydrochloride having a purity of at least 95%.

6. The method of claim 5, wherein administration of amorphous lercanidipine hydrochloride results in a in a lowering of the patients blood pressure by 25/15 mmHg (SBP/DBP) within a period of time from about 45 to about 75 minutes following administration.

7. A method of providing rapid onset of relief from hypertension in a patient, comprising the step of administering to a patient in need thereof a therapeutically effective amount of amorphous lercanidipine hydrochloride having a purity of at least 95%, wherein administration of amorphous lercanidipine hydrochloride results in a peak plasma concentration of lercanidipine ($C_{max}$) from about 10 ng/mL to about 20 ng/mL, within a period of time ($T_{max}$) from about 45 to about 75 minutes following said administration.

8. The method of claim 7, wherein $T_{max}$ within about 1 hour following said administration.

9. The method of claim 7, wherein $C_{max}$ is at least about 10 ng/mL.

10. The method any one of claim 5 or 7, wherein said therapeutically effective amount is between about 5 to about 40 mg of amorphous lercanidipine hydrochloride.

11. The method according to any one of claim 5 or 7, wherein said patient is a human.

12. A method for preparing substantially pure amorphous lercanidipine hydrochloride having a purity of at least 95% comprising,
 a) dissolving crystalline lercanidipine hydrochloride in an organic solvent at a first temperature to obtain a first solution;
 b) adding the first solution to water at a second temperature to form a second solution maintained at the second temperature for a first interval of time; and
 c) isolating the of amorphous lercanidipine hydrochloride having a purity of at least 95%.

13. The process according to claim 12, wherein said organic solvent is methanol.

14. The process according to claim 12, wherein said first temperature is in the range from about 30° C. to about 50° C.

15. The process according to claim 12, wherein said second temperature is in the range from about 1° C. to about 10° C.

16. The process according to claim 12, wherein said first interval of time is in the range from about 4 to about 24 hours.

17. A method for preparing lercanidipine hydrochloride in an amorphous form having a purity of at least 95% comprising the steps of:
 a) dissolving crystalline lercanidipine hydrochloride in an organic solvent at a first temperature to obtain a solution;
 b) evaporating the organic solvent; and c) isolating the amorphous lercanidipine hydrochloride having a purity of at least 95%.

18. An immediate release pharmaceutical composition comprising amorphous lercanidipine hydrochloride having a purity of at least 95%, a carrier, a binder, a lubricant, a disintegrant and optionally, a film coating.

19. The immediate release composition of claim 18, wherein administration of the composition to a patient results in wherein administration of amorphous lercanidipine hydrochloride results in a lowering of the patients blood pressure by 25/15 mm Hg (SBP/DBP) within a period of time from about 45 to about 75 minutes following administration.

20. The immediate release composition of claim 18, wherein administration of the composition to a patient results in a peak plasma concentration of lercanidipine ($C_{max}$) from about 10 ng/mL to about 20 ng/mL, within a period of time ($T_{max}$) from about 45 to about 75 minutes following administration.

21. A modified release composition comprising an inert core, amorphous lercanidipine hydrochloride having a purity of at least 95%, a hydrophilic polymer and optionally a film coating.

22. A modified release composition comprising amorphous lercanidipine hydrochloride having a purity of at least 95%, and a waxy substance.

* * * * *